United States Patent [19]

Schulz

[11] Patent Number: 4,501,582

[45] Date of Patent: Feb. 26, 1985

[54] PERFUSION KIT

[76] Inventor: Volker Schulz, Laudahnstrasse 37, Koln 41, Fed. Rep. of Germany

[21] Appl. No.: 558,566

[22] Filed: Dec. 5, 1983

Related U.S. Application Data

[63] Continuation of Ser. No. 328,208, Dec. 7, 1981, abandoned.

[30] Foreign Application Priority Data

Dec. 20, 1980 [DE] Fed. Rep. of Germany ....... 3048211

[51] Int. Cl.³ .............................................. A61M 5/00
[52] U.S. Cl. ...................................... 604/52; 604/56; 604/88; 604/92; 206/570
[58] Field of Search .................................... 604/51–53, 604/56, 80–92, 416; 200/570, 572

[56] References Cited

U.S. PATENT DOCUMENTS 3,857,423  7/1973  Ronca ............................... 604/56 X
4,128,173  12/1978  Lazarus et al. ..................... 206/570
4,233,973  11/1980  Shukla .................................. 604/84

OTHER PUBLICATIONS

Intensivmed. 16, 320–325, (1979), and English translation, (Shulz).
Klin. Wochenschr. 57, 905–907, (1979), (Shulz et al.).
Nieren- und Hochdruckkrankheiten, Jahrg. 10, Nr. 2/1981, S. 68–75.

*Primary Examiner*—Dalton L. Truluck

[57] ABSTRACT

A kit for the perfusion of sodium nitroprusside and sodium thiosulfate contains as components (1) a container of sodium thiosulfate aqueous solution, (2) a light-opaque syringe, (3) light-opaque tubing, and (4) an ampoule containing lyophilized sodium nitroprusside. Alternatively the kit includes (1) a light-opaque container of mixed sodium nitroprusside-sodium thiosulfate solution, (2) a light-opaque syringe, and (3) light-opaque tubing.

4 Claims, No Drawings

PERFUSION KIT

This application is a continuation of Ser. No. 328,208, filed Dec. 7, 1981, now abandoned.

Sodium nitroprusside has been commercially available since 1975 as a drug for use in humans under the trade names Nipruss (Pharma Schwarz) and Nipride (Hoffmann-LaRoche). Both products consist of dry ampoules containing 50 to 60 mg. of lyophilizate which is to be dissolved in specified commercially available infusion solutions. In dissolved form, it is then administered as an intravenous continuous infusion. The lowering of blood pressure occurs within a few minutes after the beginning of the infusion and ceases equally rapidly upon discontinuance of the infusion. The blood pressure lowering is proportional to the dose rate.

Because of its extraordinarily great effect and its good stability, sodium nitroprusside, especially as a hypotensive for emergency cases, is an indispensible drug and has been recognized as such since 1975 in the WHO list of essential drugs.

Sodium nitroprusside consists of 44% by weight of cyanide ions. The cyanide ions are liberated in blood and can lead to cyanide poisoning depending upon the dose rate and duration of infusion. In recent years several cases of fatal poisoning have become known which were caused by nitroprusside therapy. A multicenter clinical study, which is presently being organized and conducted by the applicant, has shown that even during brief administrations of nitroprusside approximately 20% of the patients are faced with dangerous accumulations of cyanide.

Animal studies have shown that cyanide detoxification in bodies is rapidly accelerated with the help of thiosulfate infusions.

Applicant has also demonstrated in its own investigations that the forced cyanide detoxification with thiosulfate is effective in patients during nitroprusside therapy. The thiosulfate dose necessary for this purpose has no harmful side effects for the patients concerned. The thiosulfate, however, must be given simultaneously with the sodium nitroprusside as an infusion because of its short biological half life. Moreover, the dose rates or flow rates of the nitroprusside and thiosulfate infusions must be adjusted to be equivalent to each other.

A summary can be found in "Intensivmed", Vol. 16 (1979), pages 320-325; in "Nieren-Und Hocherdruck Krankheiten", Vol 9, No. 6/1980; and in "Klinische Wochenschrift", Vol. 57 (1979), pages 905-907.

The proportional infusion of nitroprusside and thiosulfate through two separate infusion systems, however, presents difficulties in clinical practice; among other problems, the dose rate or flow rate of the nitroprusside infusion during the course of treatment must be adjusted very frequently according to changing blood pressure. However, the infusion of a proportionate mixed solution of both nitroprusside and thiosulfate cannot be carried out with conventional infusion apparatus because the mixed solution is light-sensitive to a high degree.

The invention has as its object the improvement of this shortcoming of the state of the art.

Investigations of applicant have shown that an aqueous mixed solution of nitroprusside and thiosulfate is stable at room temperature for a week in the total absence of visible light without loss of pharmacological effectiveness. On the basis of his investigations of doses and in the light of presently clinically available infusion apparatus, applicant has shown the effectiveness of the following mixed solutions with a significant number of patients:

Sodium Thiosulfate: 500 mg.
Sodium Nitroprusside: 50 mg.
Distilled Water: to 50 ml.

This mixed solution was prepared in conventional manner with total exclusion of light and infused into patients without exposure to light. In comparison with aqueous solutions of equal concentration of sodium nitroprusside without thiosulfate, the effect of the mixed solution in decreasing blood pressure was more intensive. This potentiating effect of the thiosulfate can possibly be explained on the basis of the previously known limitation of the nitroprusside effect through accumulation of cyanide. The cyanide concentrations in the blood increased in patients during the infusion of the mixed solution to less than 1/10 of the level which was measured upon infusion of equivalent amounts of nitroprusside in the absence of thiosulfate. Cyanide poisoning in the case of nitroprusside therapy is consequently no longer possible in the case of infusion as a mixed solution with thiosulfate.

The present invention ensures greatly improved safety in the clinical administration of nitroprusside through intravenous infusion by providing a kit comprising a system opaque to visible light for infusion of sodium nitroprusside-sodium thiosulfate mixed solution. The sodium nitroprusside-sodium thiosulfate perfusion kit of the invention consequently contains the following components:

1. Sealed container of sodium thiosulfate solution, preferably with penetrable closure;
2. Perfusion syringe of light-opaque plastic preferably with attached channel or cannula for conducting the solution;
3. Perfusion tubing of light-opaque plastic material adapted to be connected to the syringe and to a conventional perfusor or catheter.
4. Dry ampoule or other sealed container of dry, preferably lyophilized sodium nitroprusside.

The kit of the invention is adapted for use with any conventional perfusor such as that available from B. Braun Instruments (San Francisco) and/or conventional catheter for intravenous insertion. The amounts of sodium thiosulfate solution and of sodium nitroprusside in the kit may vary over as wide a range as is desired or convenient to provide the usual and conventional size dose of sodium nitroprusside, the rate of infusion being adjustable in accordance with conventional practice in administration of sodium nitroprusside. For best results the relative anhydrous weights of sodium nitroprusside and of sodium thiosulfate in the kit should be approximately 1:10±10%, but the anhydrous weight ratio of sodium nitroprusside to sodium thiosulfate may vary from 1:3 to 1:20 in certain cases. The concentration of sodium thiosulfate in aqueous solution is preferably about 1% by weight since this makes possible a convenient rate of infusion to achieve the desired dose rate. Higher or lower concentrations can also be employed, from 0.1% to 10% by weight with suitable adjustment of the flow rate or rate of infusion to achieve the desired dosage rate in accordance with conventional practice for intravenous infusion of sodium nitroprusside, up to 10 $\mu$g sodium nitroprusside per kg of body weight per minute or, particularly in the case of young persons, even higher.

In a preferred embodiment, the kit of the present invention comprises the following components:

1. Container, e.g., flask or a bottle containing 50 ml. of 1% aqueous sodium thiosulfate solution provided with a penetrable closure;
2. A 50 ml. perfusion syringe of light opaque plastic material with attached channel or cannula for delivery of the solution;
3. Perfusion tubing of light opaque plastic material;
4. Dry ampoule containing 50 mg. lyophilized sodium nitroprusside.

The kit of this embodiment is used as follows:

The thiosulfate solution is introduced into the light-opaque perfusion syringe through its attached cannula. The contents of the nitroprusside ampoule are dissolved in the ampoule with a small portion of the contents of the syringe, then immediately drawn back into the syringe and shaken therein. The light opaque tubing is attached and air is removed from the system with the syringe in vertical position. The syringe is applied to the perfusor, the latter is adjusted for a brief moment with a rapid flow rate until the end of the tube drips. Then the end of the tube is connected over a T- bar directly to the Venus catheter in a bypass in a running infusion to the patient. For the infusion, any conventional infusion solutions can be used; the flow rate should be 20 ml. per hour or more in order to avoid delayed blood pressure adjustment. The perfusion introduction begins at 1 ml./hr. and is increased according to need.

In another embodiment of the invention the sodium nitroprusside-sodium thiosulfate perfusion kit can comprise the following components:

1. Light-opaque flask or container, preferably with penetrable closure, containing a mixed aqueous solution of sodium thiosulfate solution and sodium nitroprusside dissolved therein;
2. Perfusion syringe of light-opaque plastic material with attached channel or cannula for delivery of the solution;
3. Perfusion tubing of light-opaque plastic material.

An example of this form of the kit contains the following components:

1. Light-opaque flask with penetrable rubber closure containing a mixed solution of 50 ml. 1% sodium thiosulfate solution and 50 mg. of sodium nitroprusside dissolved therein;
2. 50 ml. perfusion syringe of light-opaque plastic material with attached channel or cannula for supplying the solution;
3. Perfusion tubing of light-opaque plastic material.

This embodiment of the invention can be used in the same way as described above except that the step of dissolving the sodium nitroprusside is omitted. Extensive clinical tests show that the kits of the present invention used as described above are effective to decrease blood pressure and that the cyanide ion concentration in the blood is markedly lower when the kits are used.

What is claimed is:

1. Sodium nitroprusside-sodium thiosulfate perfusion kit comprising the following components:
   1. a sealed container of sodium thiosulfate aqueous solution, said container having a penetrable closure,
   2. a syringe of light-opaque material with attached cannula adapted to penetrate said closure, to obtain a prescribed volume of said solution,
   3. perfusion tubing of light-opaque plastic material adapted to be attached to said syringe, and
   4. a sealed container of dry solid sodium nitroprusside adapted to be dissolved by said aqueous solution to form a mixed stable aqueous solution in said syringe, the amount of said sodium nitroprusside being from $\frac{1}{3}$ to 1/20 of the weight of said sodium thiosulfate present in said solution in said syringe, wherein said mixed stable aqueous solution may be safely injected into a patient.

2. Sodium nitroprusside-sodium thiosulfate perfusion kit comprising the following components:
   1. a sealed container of light-opaque material containing a mixed stable aqueous solution of sodium thiosulfate and sodium nitroprusside, said container having a penetrable closure,
   2. a syringe of light-opaque material with attached cannula adapted to penetrate said closure, to obtain a prescribed volume of said mixed aqueous solution, and
   3. perfusion tubing of light-opaque plastic material adapted to be attached to said syringe wherein said stable mixed aqueous solution may be safely injected into a patient.

3. The method of administering to a patient a mixed stable aqueous solution of sodium nitroprusside and sodium thiosulfate which comprises forming said solution within a syringe of light-opaque material and attaching said syringe containing said solution by means of light-opaque tubing to a perfusor or catheter for intravenous delivery of said solution to said patient.

4. The method as claimed in claim 3 in which the concentration of sodium thiosulfate in said mixed solution is from 0.1 to 10% by weight and in which the weight ratio of sodium nitroprusside to sodium thiosulfate is from 1:3 to 1:20.

* * * * *